(12) United States Patent
Peultier

(10) Patent No.: US 9,084,642 B2
(45) Date of Patent: Jul. 21, 2015

(54) SPINAL IMPLANT SYSTEM AND METHOD

(75) Inventor: Bertrand Peultier, Les Hopitaux Neufs (FR)

(73) Assignee: Warsaw Orthopedic, Inc., Warsaw, IN (US)

( * ) Notice: Subject to any disclaimer, the term of this patent is extended or adjusted under 35 U.S.C. 154(b) by 241 days.

(21) Appl. No.: 13/611,414

(22) Filed: Sep. 12, 2012

(65) Prior Publication Data

US 2014/0074105 A1 Mar. 13, 2014

(51) Int. Cl.
*A61B 17/70* (2006.01)

(52) U.S. Cl.
CPC ......... *A61B 17/7082* (2013.01); *A61B 17/7083* (2013.01); *A61B 17/7091* (2013.01)

(58) Field of Classification Search
CPC ............. A61B 17/683; A61B 17/8869; A61B 17/7076; A61B 17/7083; A61B 17/7086; A61B 17/7077; A61B 17/7091
USPC .......................................................... 29/280
See application file for complete search history.

(56) References Cited

U.S. PATENT DOCUMENTS

| | | | |
|---|---|---|---|
| 3,827,470 A | 8/1974 | Douglas et al. | |
| 4,611,581 A * | 9/1986 | Steffee ........................... | 606/292 |
| 5,782,831 A * | 7/1998 | Sherman et al. ............ | 606/86 A |
| 6,440,133 B1 * | 8/2002 | Beale et al. .................. | 606/86 A |
| 6,648,888 B1 * | 11/2003 | Shluzas ....................... | 606/86 A |
| 6,761,722 B2 * | 7/2004 | Cole et al. ........................ | 606/74 |
| 7,572,281 B2 * | 8/2009 | Runco et al. .................. | 606/279 |
| 7,909,835 B2 * | 3/2011 | Oribe et al. .................... | 606/104 |
| 8,377,065 B2 * | 2/2013 | Kuntz et al. ................. | 606/86 A |
| 8,632,551 B2 * | 1/2014 | Schwer et al. ................ | 606/105 |
| 8,728,133 B2 * | 5/2014 | Fell et al. ...................... | 606/320 |
| 8,764,756 B2 * | 7/2014 | Jones ........................... | 606/86 A |
| 8,900,240 B2 * | 12/2014 | White et al. ................. | 606/86 A |
| 8,932,296 B2 * | 1/2015 | Neary et al. ................. | 606/86 A |
| 8,932,336 B2 * | 1/2015 | Nardini et al. ................. | 606/300 |
| 2004/0097941 A1 * | 5/2004 | Weiner et al. ................... | 606/72 |
| 2004/0260289 A1 * | 12/2004 | Padget et al. .................... | 606/67 |
| 2008/0045950 A1 * | 2/2008 | Dewey ............................. | 606/61 |
| 2009/0228054 A1 * | 9/2009 | Hoffman et al. ............ | 606/86 A |
| 2009/0254094 A1 | 10/2009 | Knapp et al. | |
| 2010/0298838 A1 | 11/2010 | Walters | |
| 2011/0202096 A1 | 8/2011 | White et al. | |
| 2012/0078308 A1 * | 3/2012 | Dziedzic et al. .............. | 606/264 |
| 2013/0150898 A1 * | 6/2013 | Wong et al. ................... | 606/279 |

FOREIGN PATENT DOCUMENTS

WO WO 2012/029025 * 3/2012

* cited by examiner

*Primary Examiner* — David Bates
(74) *Attorney, Agent, or Firm* — Sorell Lenna & Schmidt LLP

(57) ABSTRACT

A surgical instrument includes a first member that defines a longitudinal axis. The first member extends between a proximal end and a distal end. The distal end is configured to engage an outer surface of a first implant. A second member includes an inner surface that defines a cavity. The cavity is configured for disposal of the first member. The second member is engageable with a second implant connected to the first implant. An actuator is connected to the first member in a configuration for moving the second member into engagement with the second implant such that the second implant axially translates along the outer surface of the first implant. Systems and methods of use are disclosed.

18 Claims, 7 Drawing Sheets

SPINAL IMPLANT SYSTEM AND METHOD

TECHNICAL FIELD

The present disclosure generally relates to medical devices for the treatment of musculoskeletal disorders, and more particularly to a surgical system for implant delivery to a surgical site and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, rods, connectors and/or bone fasteners can be delivered to a surgical site. This disclosure describes an improvement over these prior art technologies.

SUMMARY

In one embodiment, in accordance with the principles of the present disclosure, a surgical instrument is provided. The surgical instrument includes a first member that defines a longitudinal axis. The first member extends between a proximal end and a distal end. The distal end is configured to engage an outer surface of a first implant. A second member includes an inner surface that defines a cavity. The cavity is configured for disposal of the first member. The second member is engageable with a second implant connected to the first implant. An actuator is connected to the first member in a configuration for moving the second member into engagement with the second implant such that the second implant axially translates along the outer surface of the first implant.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
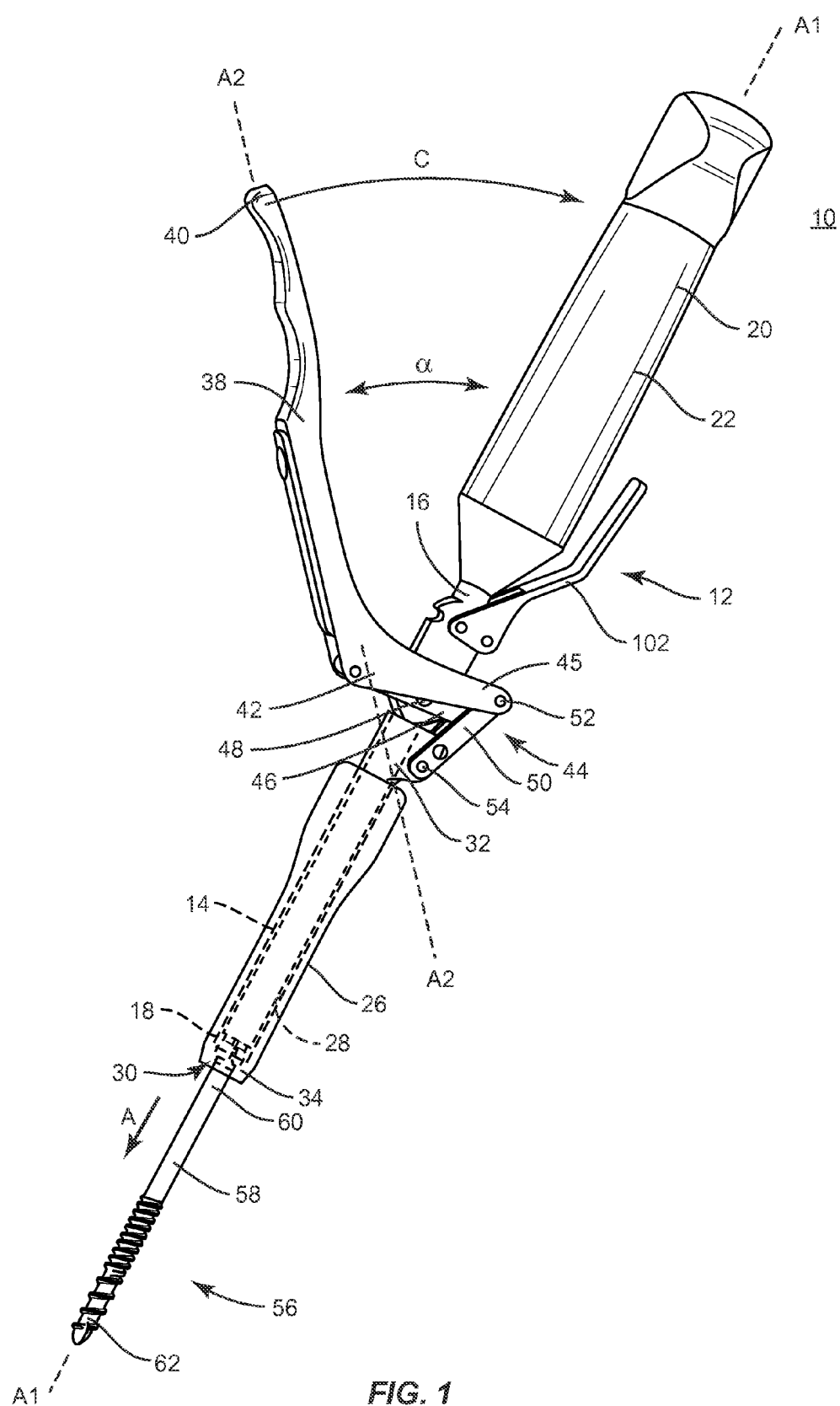
FIG. 1 is a perspective view of one embodiment of a system in accordance with the principles of the present disclosure.
Figure 2:
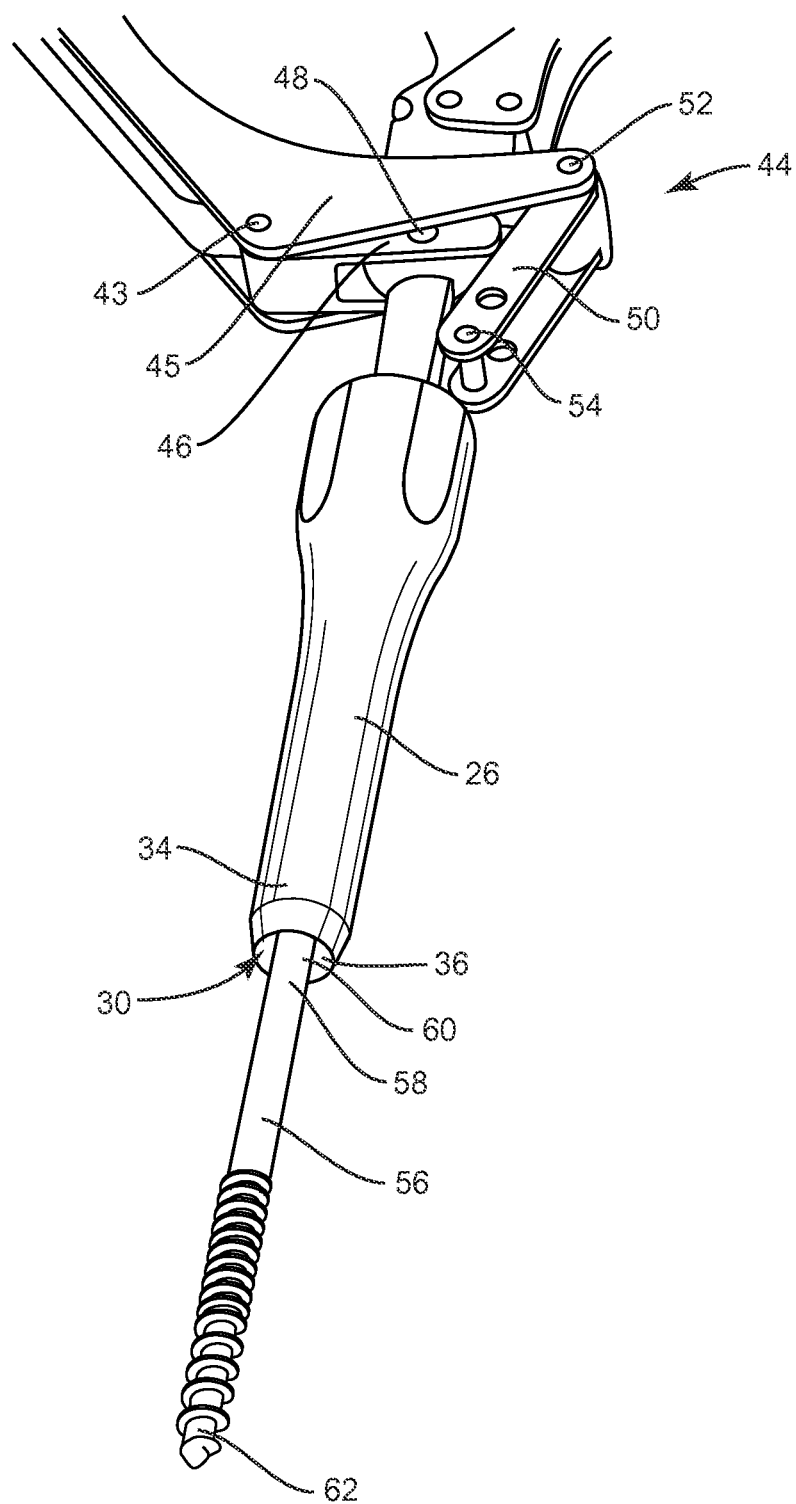
FIG. 2 is a break away perspective view of components of the system shown in FIG. 1.

The exemplary embodiments of the surgical system and related methods of use disclosed are discussed in terms of medical devices for the treatment of musculoskeletal disorders and more particularly, in terms of a surgical system for implant delivery to a surgical site and a method for treating a spine.

In one embodiment, the system is employed to treat deformities of the spine and includes an instrument used with smooth posted screws. In one embodiment, the instrument causes a connector to slide down to a spine for a dorsal reduction procedure and/or an anterior-posterior (A/P) reduction procedure. In one embodiment, the instrument pinches a top of a screw post and presses down a connector in a single maneuver that is ergonomically designed. In one embodiment, a tip of the instrument is adapted to connect to a nut disposed axial to a screw post for tightening a connector. In one embodiment, the instrument includes a reducer that connects to an axial nut of a connector. It is envisioned that the reducer instrument can both tighten and release the connector.

In one embodiment, the instrument includes a dorsal adjustment driver that causes A/P translation of a connector in a single pump motion. It is envisioned that a single pump of a handle accomplishes A/P translation of the connector. In one embodiment, the instrument includes an integrated nut driver. In one embodiment, the instrument includes a ratchet for incremental translation and/or rotation.

In one embodiment, one or all of the components of the system are disposable, peel-pack, pre-packed sterile devices used with an implant. One or all of the components of the system may be reusable. The system may be configured as a kit with multiple sized and configured components.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed system and methods may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, vessels, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference will now be made in detail to the exemplary embodiments of the present disclosure, which are illustrated in the accompanying figures. Turning now to FIGS. 1-4, there is illustrated components of a surgical system, such as, for example, a surgical implant system 10 in accordance with the principles of the present disclosure.

The components of system 10 can be fabricated from biologically acceptable materials suitable for medical applications, including metals, synthetic polymers, ceramics and bone material and/or their composites, depending on the particular application and/or preference of a medical practitioner. For example, the components of system 10, individually or collectively, can be fabricated from materials such as stainless steel alloys, aluminum, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 10 may have material composites, including the above materials, to achieve various desired characteristics such as strength, rigidity, elasticity, compliance, biomechanical performance, durability and radiolucency or imaging preference. The components of system 10, individually or collectively, may also be fabricated from a heterogeneous material such as a combination of two or more of the above-described materials. The components of system 10 may be monolithically formed, integrally connected or include fastening elements and/or instruments, as described herein.

System 10 is employed, for example, with a minimally invasive procedure, including percutaneous techniques, mini-open and open surgical techniques to deliver and introduce an implant, such as, for example, a rod, at a surgical site within a body of a patient, for example, a section of a spine. It is envisioned that system 10 may include and/or deliver and introduce implants such as bone fasteners, connectors, plates and interbody devices.

System 10 includes a surgical instrument 12 having a first member, such as, for example, a shaft 14. Shaft 14 defines a first axis A1 and extends between a proximal end 16 and a distal end 18. Proximal end 16 includes a handle 20 defining a gripping surface 22 for manipulating instrument 12 and/or fastening a bone fixation element, such as, for example, a bone screw with tissue, such as, for example, vertebrae. Distal end 18 is configured to engage an outer surface of a first implant, as discussed below.

Figure 3:
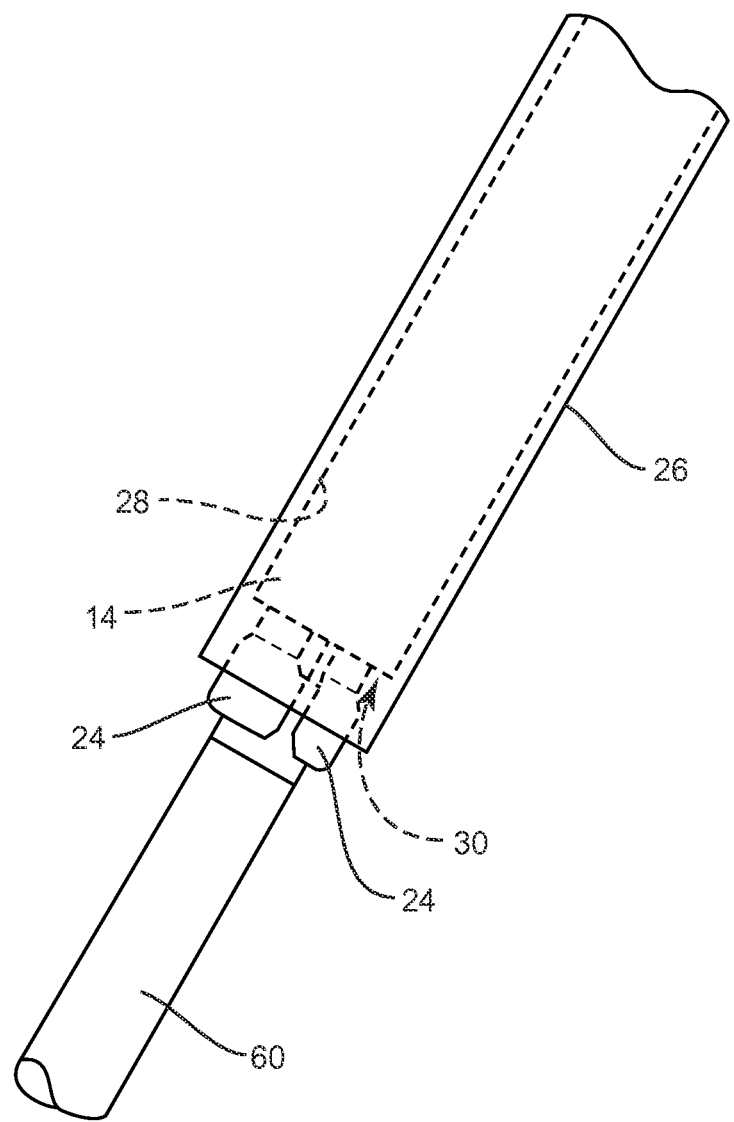
FIG. 3 is a break away perspective view of components of the system shown in FIG. 1.

Proximal end 16 includes an actuator, described herein, which is attached for pivotal movement relative thereto. Distal end 18 includes at least two capture members 24, as shown in FIG. 3. A link (not shown) extends through shaft 14 and connects capture members 24 with proximal end 16. Capture members 24 are caused to translate and engage a portion of shaft 14 to move capture members 24 between an expanded configuration and a contracted configuration to engage the outer surface of the first implant. In one embodiment, capture members 24 translate relative to an outer portion of shaft 14 between the expanded configuration such that capture members 24 extend distally beyond distal end 18 and a contracted configuration such that capture members 24 are recessed within distal end 18 to capture an implant. In one embodiment, capture members 24 may be spring biased to capture an implant. It is envisioned that one or all of the surfaces of shaft 14 and/or capture members 24 have alternate surface configurations, such as, for example, rough, threaded for connection with surgical instruments, arcuate, undulating, porous, semi-porous, dimpled, polished and/or textured according to the requirements of a particular application. It is contemplated that instrument 12 may include one or a plurality of capture members 24.

It is contemplated that shaft 14 or portions thereof can have various dimensions, for example, with regard to length, width, diameter, and thickness. Shaft 14 has a cylindrical cross section configuration. It is further contemplated that other engaging structures may be located on shaft 14, such as, for example, a nail configuration, barbs, expanding elements, raised elements and/or spikes to facilitate engagement of the implant with tissue, such as, for example, vertebrae.

A second member, such as, for example, a sleeve 26 includes an inner surface 28. It is contemplated that surface 28 may have a uniformly increasing or decreasing taper, arcuate, staggered and/or offset portions Inner surface 28 defines a cavity, such as, for example, a passageway 30. Passageway 30 is configured for moveable disposal of shaft 14. Sleeve 26 extends between and a first end 32 and a second end 34. Sleeve 26 is engageable with an outer surface of a second implant, as discussed below. End 34 includes a socket 36 for engagement with an implant. It is contemplated that one or all of the surfaces of sleeve 26 may have alternate surface configurations, such as, for example, rough, threaded for connection with surgical instruments, arcuate, undulating, porous, semi-porous, dimpled, polished and/or textured according to the requirements of a particular application.

An actuator is disposed and/or connected with shaft 14 and/or sleeve 26. The actuator includes a handle 38 extending between a first end 40 and a second end 42. The actuator is engaged to dispose sleeve 26 between a first orientation and a second orientation.

In one embodiment, the actuator includes a ratchet gear configuration that facilitates incremental axial translation of the second implant. Sleeve 26 includes a gear surface (not shown), such as, for example, a rack and shaft 14 includes gear surface (not shown) configured to engage the rack to form a ratchet gear system. The ratchet is actuated by handle 38 and the actuator to incrementally translate sleeve 26 via pumping of handle 38. As handle 38 is pumped, sleeve 26 incrementally translates along shaft 14. The ratchet system allows for axial translation in the direction shown by arrow A in FIG. 1 and prevents translation in the opposite direction shown by arrow B in FIG. 4.

The actuator includes a linkage actuator 44 connected with handle 38. Linkage actuator 44 includes a link 45 attached to handle 38 at a pivot 43. A first link 46 is connected to link 45 at pivot 43 and proximal end 16 of shaft 14 at a pivot point 48. A second link 50 is connected to link 45 at a pivot point 52. Link 50 is connected to first end 32 of sleeve 26 at a pivot point 54.

The actuator defines a second axis A2 along handle 38 disposed at an angular orientation relative to axis A1. The actuator as facilitated by linkage actuator 44 is configured to initially move shaft 14 to compress and/or contract capture members 24 and engage the outer surface of an implant. Linkage actuator 44 is moveable between a first orientation and a second orientation to initially translate shaft 14 relative to capture members 24, and thereafter translate sleeve 26 relative to shaft 14. Handle 38 is employed to move linkage actuator 44 for rotation of its links to initially drive shaft 14 relative to capture members 24, and thereafter drive sleeve 26 in an axial direction between a first orientation, as shown in FIG. 1, and a second orientation, as shown in FIG. 4.

Figure 4:
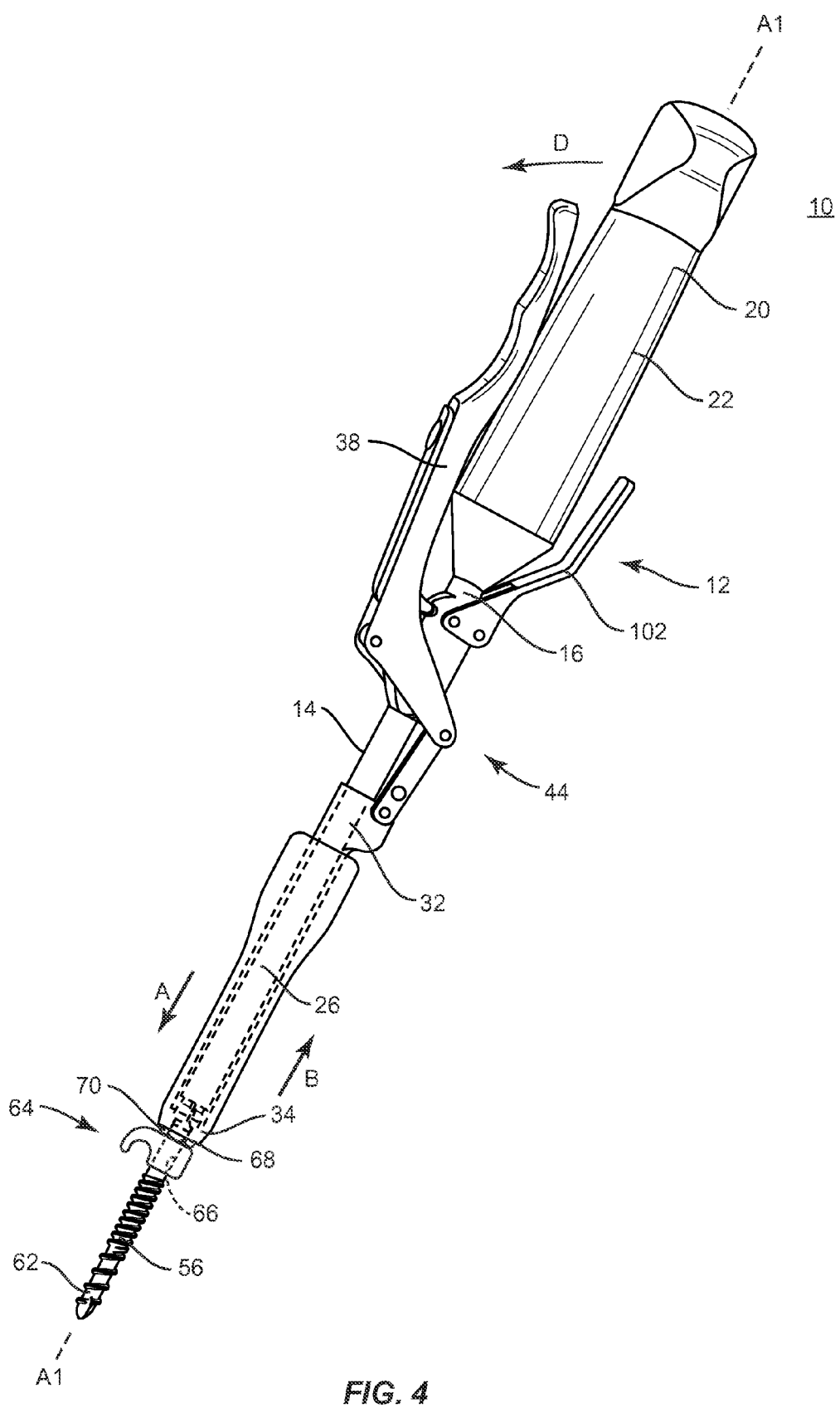
FIG. 4 is a perspective view of the system shown in FIG. 1.

Handle 38 is engaged with shaft 14 and sleeve 26, via actuator 44, such that shaft 14 axially translates relative to capture members 24 and sleeve 26 axially translates relative to shaft 14, in a first direction, such as, for example, the direction shown by arrow A in FIGS. 1 and 4, and a second direction, such as, for example, in the direction shown by arrow B in FIG. 4. In the first orientation, axis A2 of handle 38 is disposed at an angular orientation α (FIG. 1) relative to axis A1, and handle 38 is spaced apart from proximal end 16. In the first orientation, sleeve 26 is disposed in a proximal most position. In the second orientation, axis A2 of handle 38 is substantially parallel to axis A1. In the second orientation, handle 38 is disposed in close proximity to proximal end 16 and sleeve 26 is disposed in a distal most position. It is contemplated that handle 38 may be disposed in one or a plurality of angular orientations corresponding angle α. In one embodiment, handle 38 is disposed at an angle α, which can be within a range of 0 to 180 degrees.

A first implant, such as, for example, a screw 56 includes a shaft 58. Shaft 58 extends between a proximal end 60 and a distal end 62. Distal end 60 is threaded along a portion of a length of shaft 58 and configured for penetrating tissue. Shaft 58 has a cylindrical cross section configuration and includes an outer surface having an external thread form. Proximal end 60 is configured for engagement with capture members 24. It is contemplated that the thread form may include a single thread turn or a plurality of discrete threads. It is further contemplated that other engaging structures may be located on shaft 58, such as, for example, a nail configuration, barbs, expanding elements, raised elements and/or spikes to facilitate engagement of shaft 58 with tissue, such as, for example, vertebrae and/or iliac bone.

It is envisioned that all or only a portion of shaft 58 may have alternate cross section configurations, such as, for example, oval, oblong, triangular, square, polygonal, irregular, uniform, non-uniform, offset, staggered, undulating, arcuate, variable and/or tapered. It is contemplated that the outer surface of shaft 58 may include one or a plurality of openings. It is further contemplated that all or only a portion of the outer surface of shaft 58 may have alternate surface configurations to enhance fixation with tissue such as, for example, rough, arcuate, undulating, mesh, porous, semi-porous, dimpled and/or textured according to the requirements of a particular application. It is envisioned that all or only a portion of shaft 58 may be disposed at various orientations, relative to axis a, such as, for example, transverse, perpendicular and/or other angular orientations such as acute or obtuse and/or may be offset or staggered. It is further envisioned that all or only a portion of shaft 58 may be cannulated.

A second implant, such as, for example, a connector 64 includes an inner surface 66. Inner surface 66 defines an opening 68. It is envisioned that all or only a portion of inner surface 66 may have alternate cross section configurations, such as, for example, oval, oblong, triangular, square, polygonal, irregular, uniform, non-uniform, offset, staggered, and/or tapered. Connector 64 is configured for engagement with a coupling member, such as, for example, a nut 70. Nut 70 is configured for engagement with socket 36. It is envisioned that connector 64 may be disposed with nut 70 in alternate fixation configurations, such as, for example, a threaded fit, friction fit, pressure fit, locking protrusion/recess, locking keyway and/or adhesive. It is contemplated that all or only a portion of connector 64, for example, inner surface 66, may have alternate surface configurations to enhance fixation with nut such as, for example, rough, arcuate, undulating, mesh, porous, semi-porous, dimpled and/or textured according to the requirements of a particular application. In one embodiment, connector 64 includes nut 70.

In operation, handle 38 is fully spaced apart from handle 20 such that handle 38 is disposed at an angular orientation, for example, angle α being equal to 45 degrees, relative to axis A1, to extend capture members 24 distally beyond distal end 18 such that capture members 24 are expanded outwardly. Handle 38 is rotated about pivot 48 in a clockwise direction, in the direction shown by arrow C, to axially translate shaft 14 in the direction shown by arrow A in FIG. 1 relative to capture members 24. Link 45 of handle 38 rotates link 46 such that link 46 rotates relative to pivot 48 and proximal end 16. In turn, link 46 initially drives shaft 14 axially, in the direction shown by arrow A, to cause capture members 24 to recess within the outer portion of shaft 14. Translation of capture members 24 into shaft 14 contracts capture members 24 such that capture members 24 clamp onto an implant, such as, for example, proximal end 60 of shaft 58. Releasable retention of shaft 58 by capture members 24 facilitates movement of nut 70 and connector 64 over shaft 58 for translation along shaft 58.

In a first orientation, sleeve 26 is disposed at its proximal most position and handle 38 is disposed at an angle α, for example, angle α is equal to 35 degrees, relative to axis A1. Socket 36 is engaged with nut 70 and connector 64.

Handle 38 is rotated about pivot 48 in a clockwise direction, in the direction shown by arrow C, to axially translate sleeve 26 in the direction shown by arrow A. Link 45 of handle 38 rotates link 46 such that link 46 rotates relative to pivot 48 and proximal end 16. Connection of link 45 to link 46 provides leverage to handle 38/link 45 such that link 45 rotates and drives second link 50 axially. In turn, link 50 drives sleeve 26 axially, in the second direction shown by arrow A. Sleeve 26 engages an implant, such as, for example, nut 70/connector 64 to axially translate nut 70/connector 64 along shaft 58.

In the second orientation, as shown in FIG. 4, handle 38, disposed along axis A2, is oriented in a substantially parallel orientation relative to axis A1, which may include angle α being equal to 10 degrees or less, relative to axis A1. Nut 70/connector 64 are driven and/or translated axially in the direction shown by arrow A along shaft 58. This configuration delivers nut 70/connector 64 to a surgical site, for example, adjacent a spinal rod for fixation of an implant system with vertebrae, as will be described. Socket 36 engages nut 70/connector with screw 56, which may be disposed in penetration with vertebrae, for fixation of the implant system with vertebrae via manipulation of handle 20, as described herein. Proximal end 16 includes a lock handle 102, which is engageable to lock engagement of socket 36 with nut 70/connector 64 and/or capture members 24 with screw 56. Handle 102 is rotatable to lock position of an implant(s) and rotatable to eject and/or release engagement with the implant(s).

Handle 38 is rotated in the direction shown by arrow D in FIG. 4, to axially translate sleeve 26 in the direction shown by arrow B, to a first orientation (FIG. 1). Socket 36 is disengaged from nut 70/connector 64. Handle 38 is further rotated in the direction shown by arrow D to extend capture members 24 distally beyond distal end 18 such that capture members 24 are expanded outwardly to eject and/or release screw 56.

Figure 5:
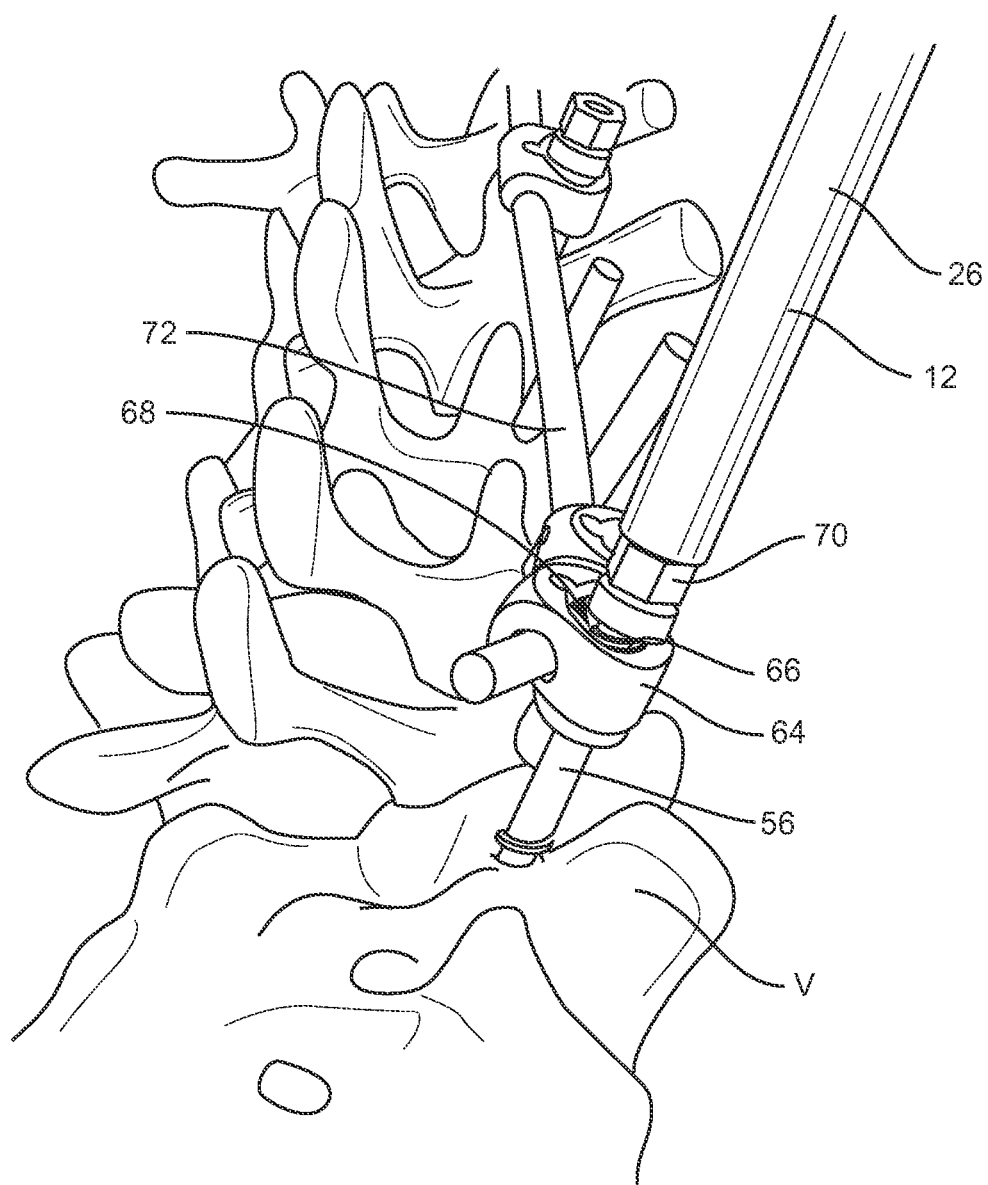
FIG. 5 is a break away perspective view of one embodiment of a system in accordance with the principles of the present disclosure disposed with vertebrae.
Figure 6:
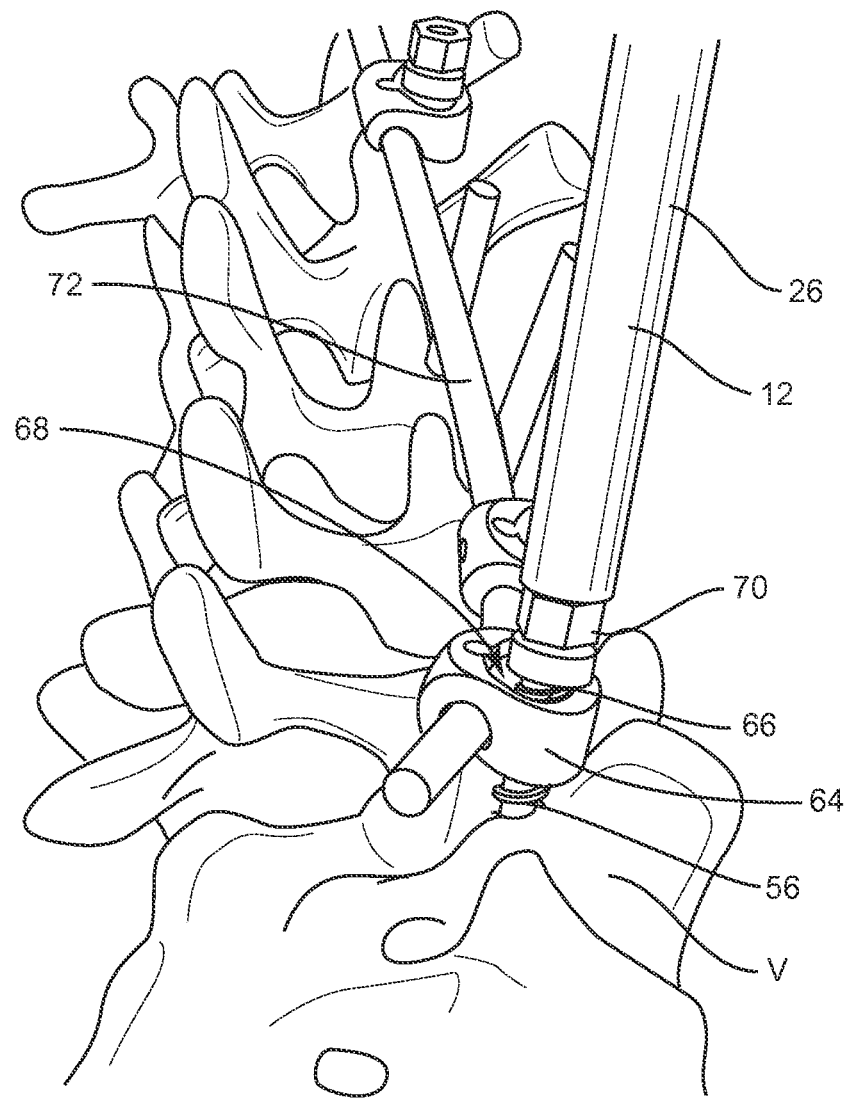
FIG. 6 is a perspective view of the system disposed with vertebrae shown in FIG. 5.
Figure 7:
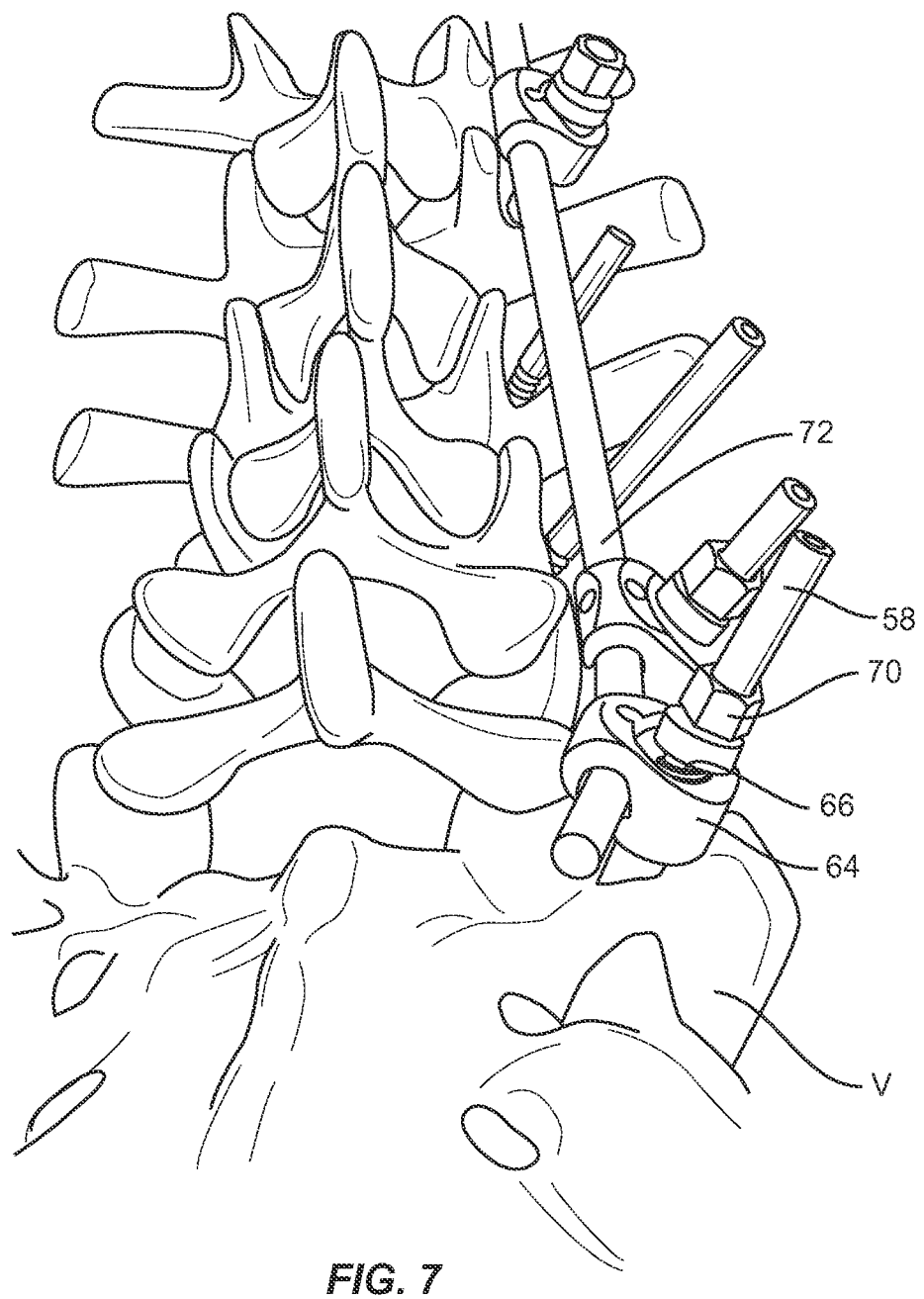
FIG. 7 is a perspective view of components of the system shown in FIG. 5 disposed with vertebrae.

In assembly, operation and use, as shown in FIGS. 5-7, spinal implant system 10 including instrument 12, similar to that described above with regard to FIGS. 1-4, is employed with a surgical procedure for treatment of a spinal disorder affecting a section of a spine of a patient, as discussed herein. Spinal implant system 10 may also be employed with other surgical procedures. For example, spinal implant system 10 can be used with a surgical procedure for treatment of a condition or injury of an affected section of the spine including vertebrae V.

In use, to treat the affected section of vertebrae V, a medical practitioner obtains access to a surgical site in any appropriate manner, such as through incision and retraction of tissues. It is envisioned that spinal implant system 10 may be used in any existing surgical method or technique including open surgery, mini-open surgery, minimally invasive surgery, and percutaneous surgical implantation, whereby vertebrae V is accessed through a micro-incision, or sleeve that provides a protected passageway to the area. Once access to the surgical site is obtained, the particular surgical procedure is performed for treating the spinal disorder. Spinal implant system 10 is then employed to augment the surgical treatment. The components of spinal implant system 10 can be delivered or implanted as a pre-assembled device or can be assembled in situ. The components of spinal implant system 10 may be completely or partially revised, removed or replaced during or after the surgical procedure.

Pilot holes or the like are made in vertebrae V for receiving screws 56. Components of spinal implant system 10 are disposed adjacent vertebrae V at a surgical site and instrument 12 is manipulable to drive, torque, insert or otherwise connect nuts 70/connectors 64, screws 56 and rods 72 with vertebrae V, according to the particular requirements of the surgical treatment.

A practitioner manipulates instrument 12 such that handle 38 is initially rotated from a fully open position, disposed at an angle α relative to axis A1, to translate shaft 14 and cause capture members 24 to recess within shaft 14 and contract such that capture members 24 clamp onto proximal end 60 of a shaft 58, as described herein. In a first orientation, as shown in FIG. 1, sleeve 26 is disposed at its proximal most position and handle 38 is disposed at an angle α relative to axis A1, as described herein. Socket 36 is engaged with nut 70 and connector 64.

Handle 38 is rotated to axially translate sleeve 26 (see arrow A in FIG. 1). Sleeve 26 engages nut 70/connector 64 to axially translate nut 70/connector 64 along shaft 58. In the second orientation (FIG. 4), handle 38, disposed along axis A2, is oriented in a substantially parallel orientation relative to axis A1. Nut 70/connector 64 are driven and/or translated axially along shaft 58. This configuration delivers nut 70/connector 64 adjacent rod 72 for fixation with rod 72 and vertebrae V. Rod 72 is fixed with connector 64. Socket 36 engages nut 70/connector 64 to fasten the components of system 10 with vertebrae V via manipulation of handle 20. Handle 20 torques nut 70 to fix connector 64 and rod 72 with vertebrae V.

Handle 38 is rotated in the direction shown by arrow D in FIG. 4, to axially translate sleeve 26 in the direction shown by arrow B, to the first orientation (FIG. 1). Socket 36 is disengaged from nut 70/connector 64. Handle 38 is further rotated in the direction shown by arrow D to extend capture members 24 distally beyond distal end 18 such that capture members 24 are expanded outwardly to eject and/or release screw 56. Upon completion of the procedure, surgical instrument 12 is removed from the surgical site. It is contemplated that the non-implant components of system 10 are removed from the surgical site and the incision is closed.

One or more of the components of system 10 can be made of radiolucent materials such as polymers. Radiomarkers may be included for identification under x-ray, fluoroscopy, CT or other imaging techniques. It is envisioned that the use of microsurgical and image guided technologies may be employed to access, view and repair spinal deterioration or damage, with the aid of system 10.

It is contemplated that system 10 may include one or a plurality of spinal rods and/or bone fasteners for use with a single vertebral level or a plurality of vertebral levels. It is further contemplated that the rods and/or bone fasteners may be engaged with vertebrae in various orientations, such as, for example, series, parallel, offset, staggered and/or alternate vertebral levels. It is envisioned that the bone fasteners may include one or a plurality of anchors, tissue penetrating screws, conventional screws, expanding screws, wedges, anchors, buttons, connectors, clips, snaps, friction fittings, compressive fittings, expanding rivets, staples, nails, adhesives, posts, fixation plates and/or posts.

In one embodiment, system 10 includes an agent, which may be disposed, packed or layered within, on or about the components and/or surfaces of system 10. It is envisioned that the agent may include bone growth promoting material, such as, for example, bone graft to enhance fixation of the fixation elements with vertebrae. It is contemplated that the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
   a first member defining a longitudinal axis and extending between a proximal end and a distal end configured to engage an outer surface of a first implant, the distal end being movable between an expanded configuration and a contracted configuration to engage the outer surface of the first implant;
   a second member including an inner surface that defines a cavity configured for disposal of the first member, the second member being engageable with a second implant connected to the first implant; and
   an actuator connected to the first member, the actuator defining a first axis, the actuator being rotatable relative to the longitudinal axis such that the actuator is movable between a first orientation in which the first axis is disposed at a first angle relative to the longitudinal axis and a second configuration in which the first axis is disposed at a reduced second angle relative to the longitudinal axis to axially translate the first member into engagement with the first implant and to axially translate the second implant axially along the outer surface of the first implant.

2. A surgical instrument of claim 1, wherein the proximal end includes a handle having a gripping surface.

3. A surgical instrument of claim 1, wherein the distal end includes at least two capture members configured to space apart and engage the outer surface of the first implant.

4. A surgical instrument of claim 1, wherein the proximal end includes a first link connected to the distal end and configured to move the distal end for engaging the outer surface of the first implant.

5. A surgical instrument of claim 1, wherein the actuator is connected to the proximal end via a linkage to allow the actuator to rotate relative to the longitudinal axis.

6. A surgical instrument of claim 5, wherein the linkage includes a first link that connects the actuator and the first member and a second link that connects the actuator and the second member.

7. A surgical instrument of claim 1, wherein the actuator extends between a first end and a second end connected with the first member.

8. A surgical instrument of claim 7, wherein the first axis is substantially parallel to the longitudinal axis when the actuator is in the second orientation.

9. A surgical instrument of claim 1, wherein:
   the actuator is spaced apart from the proximal end and the second member is disposed in a proximal most position when the actuator is in the first configuration; and
   the actuator is disposed in close proximity to the proximal end and the second member is disposed in a distal most position when the actuator is in the second configuration.

10. A surgical instrument of claim 1, wherein the second member extends between a first end and a second end configured for engagement with an outer surface of the second implant.

11. A surgical instrument of claim 1, wherein the second implant includes a nut engageable with the second member and a connector connected with the first implant.

12. A surgical instrument of claim 1, wherein the actuator includes a ratchet configured to facilitate incremental axial translation of the second implant.

13. A surgical instrument comprising:
    a shaft defining a first axis and extending between a proximal end including a gripping surface and a distal end configured to engage an outer surface of a first implant, the distal end being movable between an expanded configuration and a contracted configuration to engage the outer surface of the first implant;
    a sleeve including an inner surface that defines a passageway configured for moveable disposal of the shaft and being engageable with an outer surface of a second implant that is connected with the first implant; and
    an actuator defining a second axis and being connected to the proximal end via a linkage such that the second axis is rotatable relative to the first axis,
    wherein the actuator is moveable between a first orientation such that the second axis is disposed at a first angular orientation relative to the first axis and a second orientation such that the second axis is disposed at a second angular orientation relative to the first axis to axially translate the shaft into engagement with the first implant and to axially translate the sleeve causing the second implant to translate along the outer surface of the first implant.

14. A surgical instrument of claim 13, wherein distal end includes at least two capture members configured to space apart and engage the outer surface of the first implant.

15. A surgical instrument of claim 13, wherein the linkage includes a first link that connects the actuator and the first member and a second link that connects the actuator and the second member.

16. A surgical instrument of claim 13, wherein the proximal end includes a first link connected to the distal end and configured to move the distal end for engaging the outer surface of the first implant.

17. A surgical instrument of claim 13, wherein the actuator includes a ratchet configured to facilitate incremental axial translation of the second implant.

18. A surgical implant system comprising:
a shaft defining a first axis and extending between a proximal end including a gripping surface and a distal end including expandable capture members;
a sleeve including an inner surface that defines a passageway configured for moveable disposal of the shaft, the sleeve extending between a first end and a second end including a socket;
an actuator defining a second axis and being connected to the shaft via a linkage such that the second axis is rotatable relative to the first axis, the linkage including a first link that connects the actuator and the proximal end and a second link that connects the actuator to the sleeve;
a screw extending between a proximal end configured for engagement with the capture members and a distal end configured for penetrating tissue; and
a connector including an inner surface that defines an opening and a nut configured for engagement with the socket,
wherein the actuator is moveable between a first orientation such that the actuator is spaced apart from the proximal end and the sleeve is disposed in a proximal most position and a second orientation such that the actuator is disposed in close proximity to the proximal end and the sleeve is translated for disposal in a distal most position so that the connector is axially translated along an outer surface of the screw.

* * * * *